United States Patent [19]

Marchi et al.

[11] Patent Number: 5,643,672
[45] Date of Patent: Jul. 1, 1997

[54] COSMETIC COMPOSITION CONTAINING SOLID PARTICLES COATED WITH AN AMPHOTERIC POLYMER

[75] Inventors: Patricia Marchi, Paris; Myriam Mellul, L'Hay-les-Rose, both of France

[73] Assignee: L'Oreal, Paris, France

[21] Appl. No.: 397,137

[22] PCT Filed: Sep. 13, 1993

[86] PCT No.: PCT/FR93/00879

§ 371 Date: May 18, 1995

§ 102(e) Date: May 18, 1995

[87] PCT Pub. No.: WO94/06407

PCT Pub. Date: Mar. 31, 1994

[30] Foreign Application Priority Data

Sep. 11, 1992 [FR] France .................. 92 10884

[51] Int. Cl.$^6$ ....................................... B32B 5/16
[52] U.S. Cl. .............. 428/402; 424/69; 514/844; 514/845; 514/846; 514/847; 514/848
[58] Field of Search ................ 428/402; 424/69; 514/844, 845, 846, 847, 848

[56] References Cited

U.S. PATENT DOCUMENTS 4,818,614  4/1989  Fukui et al. ......................... 428/403

FOREIGN PATENT DOCUMENTS

| 209879 | 1/1987 | European Pat. Off. . |
| 212870 | 3/1987 | European Pat. Off. . |
| 220617 | 5/1987 | European Pat. Off. . |
| 2234359 | 1/1975 | France . |
| 2339656 | 8/1977 | France . |
| 2107186 | 4/1983 | United Kingdom . |

*Primary Examiner*—Terressa Mosley
*Attorney, Agent, or Firm*—Cushman Darby & Cushman Intellectual Property Group of Pillsbury Madison & Sutro L.L.P.

[57] ABSTRACT

Cosmetic composition for the skin or skin appendages comprising a dispersion of solid particles in a binder and characterized in that at least a part of said particles is introduced into the composition in the form of particles having their surface coated with at least one amphoteric polymer. The coated particles are easily dispersible, even in fatty binders, and the cosmetic compositions have good stability properties and show good adhesion to the skin and skin appendages.

31 Claims, No Drawings

COSMETIC COMPOSITION CONTAINING SOLID PARTICLES COATED WITH AN AMPHOTERIC POLYMER

BACKGROUND OF THE INVENTION

1. Field of the Invention

The present invention relates to cosmetic compositions for the skin or the exoskeleton containing a dispersion of solid particles whose surface is coated by means of an amphoteric polymer.

2. Background Information

Various make-up products, such as loose or compact powders, make-up foundations, blushers, eyeshadows and also lipsticks, are known to be presented in the form of compositions comprising a dispersion of solid inorganic particles in a fatty binding agent. The products in question can be anhydrous compositions or alternatively oil-in-water or water-in-oil emulsions.

Depending on the type of composition, the solid particles are exclusively pigments (white and/or coloured) intended to impart a certain coloration to the skin of the face or lips, or particles, generally referred to as "fillers", which have diverse functions which vary with the nature of the particles.

In compositions for application to the skin, use is often made of fillers intended to provide a covering power, that is to say to mask skin imperfections (differences in coloration, minor unevenness), either as a result of their opacity (this applies, in particular, to titanium oxide, zinc oxide and kaolin), or through their properties of reflection of light (this applies, in particular, to lamellar fillers such as talc and micas). Fillers are also used which are capable of absorbing the aqueous and oily secretions of the skin, in order to avoid a glistening appearance of the skin and the migration of colorants: kaolin, starch, precipitated calcium carbonate, bentonite and the like, are, for example, employed for this purpose.

Use is also made, in compositions intended for protection against UV radiation, of particles, micronized or otherwise, of $TiO_2$ and of ZnO as ultraviolet-absorbing agents.

In lipsticks, the solid particles dispersed in a suitable fatty binding agent are mostly coloured pigments, optionally in combination with white pigments (for example fine particles of titanium dioxide) which enable the shades of the colours provided by the coloured pigments to be varied.

Such white and/or coloured pigments are also used in nail varnish compositions, which consist essentially of a dispersion of these pigments in a solution of a film-forming polymer and a plasticizer in a suitable organic solvent.

The preparation and use of cosmetic compositions containing dispersions of solid particles create several kinds of problem. One problem common to the production of all the compositions just mentioned lies in the difficulty of obtaining homogeneous and stable dispersions, so as to apply, for example to the skin, an even make-up whose application is uniform and which retains good homogeneity. This requirement has led the experts to perform surface treatments on the powders used, in particular in order to modify the interfacial properties participating in the phenomena of wetting and dispersion. The aim of these treatments is often to make the powder hydrophobic in order to promote its incorporation in the formulation binding agents and oils, and to increase the stability of the dispersion by decreasing flocculation and aggregation phenomena; see, for example, European Patent 279,319, which describes the coating of pigments with silicone polymers.

Dispersion of the solid particles in aqueous media also gives rise to difficulties and, in order to overcome these, dispersing agents which are introduced into the dispersion medium are used in particular. Thus, for example, Patent FR 2,655,875 relates to the use of amphoteric copolymers as dispersing agents, especially in the papermaking field, and Patent FR 2,550,795 describes a pigment composition for paints containing an amphoteric dispersing resin. These various treatments hence enable the problems of stability of the dispersion to be resolved by limiting the flocculation phenomena. However, they do not resolve another major problem, namely the poor properties of adhesion of the solid particles to the skin. In effect, it is known that the solid particles used, in particular, in compositions in powder form have only poor properties of adhesion to the skin. The surface treatments intended to improve the stability of the dispersions in the fatty binding agents do not provide a substantial improvement as regards the adhesion properties.

SUMMARY OF THE INVENTION

It has now been discovered that it is possible to obtain cosmetic compositions comprising a dispersion of solid particles in a binding agent, having good properties of stability and adhesion to the skin or to the exoskeleton, by introducing into the said compositions solid particles whose surface has been coated with an amphoteric polymer. It was found, surprisingly, that the coating of solid particles with amphoteric polymers, which constitute, however, a hydrophilic coating, does not prevent a good dispersibility of the particles in fatty binding agents from being obtained. Moreover, the compositions thereby obtained have good properties of adhesion to the skin after application. The adhesion to the skin is not excessive, and hence permits a distribution on the skin and a make-up result which are especially homogeneous.

In addition, the coating of solid particles with an amphoteric polymer is compatible with the use of cationic polymers in cosmetic compositions containing such coated particles.

Moreover, the coated particles according to the invention retain their amphoteric character even after application to the skin, and irrespective of the nature of the particle thus coated.

The optimal quantitative ratio of cationic groups to anionic groups ranges from 40:60 to 90:10.

DETAILED DESCRIPTION OF THE INVENTION

The subject of the present invention is hence a cosmetic composition for the skin or the exoskeleton comprising a dispersion of solid particles in a binding agent, characterized in that at least a part of the said particles is introduced into the said composition in the form of particles whose surface is coated with at least one amphoteric polymer.

In the compositions of the invention, solid particles are surface-coated with an amphoteric polymer. This means that, after coating, there is neither a change in morphology nor a significant modification of the sizes of the particles, as may be verified by electron-microscopy.

In the present application, the term "amphoteric polymer" denotes a polymer containing both cationic and anionic groups and/or groups which can ionize to cationic and anionic groups, respectively.

The amphoteric polymers are known products.

Preferred cationic groups are chosen from those which contain primary, secondary, tertiary and/or quaternary amine groups, which can either form part of the polymer chain or be carried by a side-chain substituent.

The cationic group is preferably chosen from primary, secondary, tertiary and/or quaternary amino groups. The anionic groups can, for example, be $COO^-$, $SO_3^-$, $PO_4^{3-}$ or $SO_4^{2-}$ groups.

These two types of charged groups (anionic and cationic) are each preferably carried by a side-chain substituent and are more or less well separated from one another.

Preferably, the cationic groups are quaternary ammonium groups, which may be obtained by quaternization of amino groups by means of traditional quaternizing agents such as alkyl or aralkyl halides (for example methyl iodide, ethyl bromide, benzyl chloride, and the like) or alkyl sulphates (for example dimethyl sulphate).

The amphoteric polymers used can have a molecular mass generally of between $10^3$ and $10^9$ approximately, and most often between $10^3$ and $10^6$.

Preferably, the coated particles used in the compositions of the invention are coated exclusively with one (or more) amphoteric polymer(s).

When the amphoteric polymer carries cationic and anionic groups on side-chain substituents, the polymer chain is, for example an acrylic, vinyl, silicone, fluorinated or saccharide chain. It is preferable to use amphoteric polymers not containing silicon, that is to say polymers other than silicones.

The amounts of polymer deposited on the particles vary with the procedure used for obtaining the coating. Generally, the weight proportion of amphoteric polymer relative to the total weight of the coated particles is equal to at least 0.1%; the upper limit to the amount of amphoteric polymer is sufficiently low for the particles to keep their individual identity and their shape. In other words, the amphoteric polymer forms, at most, a thin layer (possibly lacunate) on the coated particles. More often than not, the weight proportion of amphoteric polymer in the coated particles is less than 10%, and preferably less than 8%, relative to the total weight of the coated particles. In fact, more often than not, an optimal result is obtained with a coating not exceeding 2% by weight. The risk of obtaining coated pigments whose colour becomes drab after coating is avoided in this way.

The compositions of the invention are, in particular, those which contain a dispersion of solid particles whose surface is coated with at least one amphoteric polymer containing units A and B distributed statistically in the polymer chain, where A denotes a unit derived from a monomer containing at least one cationic group as defined above, and B denotes a unit derived from a monomer containing one or more anionic groups, in particular carboxyl or sulphonic groups, or alternatively A and B, which may be identical or different, represent a group derived from a carboxybetaine zwitterionic monomer; A and B can also denote a polymer chain containing secondary, tertiary or quaternary amine groups, in which chain at least one of the amine groups carries a carboxyl or sulphonic substituent attached via a hydrocarbon arm, or alternatively A and B form part of a polymer chain containing ethylene-alpha, beta-dicarboxyl units in which one of the carboxyl groups has reacted with a polyamine containing one or more primary or secondary amine groups.

The amphoteric polymers corresponding to the definition stated above are chosen, in particular, from the following polymers:

(1) polymers resulting from the copolymerization of a monomer derived from a vinyl compound carrying a carboxyl group, such as acrylic acid, methacrylic acid, maleic acid and alpha-chloroacrylic acid, and a basic monomer derived from a substituted vinyl compound containing at least one basic nitrogen atom, such as dialkylaminoalkyl methacrylates and acrylates and dialkylaminoalkyl-methacrylamides and-acrylamides. Such compounds are described in U.S. Pat. No. 3,836,537.

(2) polymers containing units derived from:

a) at least one monomer chosen from acrylamides or methacrylamides substituted on the nitrogen with an alkyl radical, b) at least one acidic comonomer containing one or more reactive carboxyl groups, and c) at least one basic comonomer such as an ester containing primary, secondary, tertiary and quaternary amine substituents of acrylic and methacrylic acids, or the product of quaternization of dimethylaminoethyl methacrylate with dimethyl or diethyl sulphate.

More especially preferred N-substituted acrylamide or methacrylamide monomers for the polymers mentioned above are, in particular, those in which the alkyl groups contain from 2 to 12 carbon atoms, and more especially N-ethylacrylamide, N-tert-butylacrylamide, N-tert-octylacrylamide, N-octylacrylamide, N-decylacrylamide, N-dodecylacrylamide or the corresponding methacrylamides. The acidic comonomers are chosen more especially from acrylic, methacrylic, crotonic, itaconic, maleic and fumaric acids, as well as the $C_1$–$C_4$ alkyl monoesters of maleic acid or fumaric acid.

The basic comonomers are, for example, aminoethyl, butylaminoethyl, N,N-dimethylaminoethyl or N-tert-butylaminoethyl methacrylates.

Among these copolymers, the products sold by the company National Starch under the name Amphomer may be mentioned.

(3) polyaminoamides, optionally partially or completely crosslinked and/or alkylated, derived from polyaminoamides containing units of general formula:

$$—[—OC—R—CO—Z—]—\qquad(I)$$

in which R represents a bivalent radical derived from a saturated dicarboxylic acid, from a mono- or dicarboxylic aliphatic acid containing an ethylenic double bond, from an ester of these acids with a lower alkanol having 1 to 6 carbon atoms or from a radical derived from the addition of any one of the said acids with a bis-primary or bis-secondary amine, and Z denotes a radical of a polyalkylenepoly(bis-primary or mono- or bis-secondary amine). In particular, in the said copolymers, Z can represent:

a) in a proportion of 60 to 100 mol % relative to the collective units containing Z, the radical

$$—NH—[—(CH_2)_x—NH—]—_n\qquad(II)$$

where x=2 and n=2 or 3, or alternatively x=3 and n=2 (this radical hence being derived from diethylenetriamine, triethylenetetramine or dipropylenetriamine), b) in a proportion of 0 to 40 mol %, the above radical (II) in which x=2 and n=1 (hence derived from ethylenediamine) or the radical

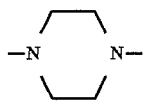

(derived from piperazine), c) in a proportion of 0 to 20 mol %, the radical —NH—(CH$_2$)$_6$—NH— (derived from hexamethylenediamine), these polyaminoamides being optionally cross-linked by the addition of a bifunctional crosslinking agent chosen from epihalohydrins, diepoxides, dianhydrides and bis-unsaturated derivatives, for example by means of 0.025 to 0.35 mol of crosslinking agent per amine group of the polyaminoamide, and/or it being possible for them to be alkylated by the action of acrylic acid, chloroacetic acid, an alkanesultone or their salts.

The saturated carboxylic acids are preferably chosen from acids having 6 to 10 carbon atoms, such as adipic and 2,2,4-and 2,4,4-trimethyladipic acids, terephthalic acid and acids containing an ethylenic double bond such as, for example, acrylic, methacrylic or itaconic acid.

The alkanesultones which can be used in the alkylation of the polyaminoamides are, for example, propane- or butanesultone, the salts of the said alkylating agents being, in particular, the sodium or potassium salts.

(4) polymers containing zwitterionic units derived from a monomer of formula:

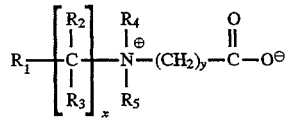

in which

R$_1$ denotes a polymerizable unsaturated group such as an acrylate, methacrylate, acrylamide or methacrylamide group, x and y independently represent an integer from 1 to 3, R$_2$ and R$_3$ represent hydrogen, methyl, ethyl or propyl, R$_4$ and R$_5$ represent a hydrogen atom or an alkyl radical, R$_4$ and R$_5$ being such that the sum of the carbon atoms they contain does not exceed 10.

The polymers comprising such units can also contain, in addition, units derived from non-zwitterionic monomers such as vinylpyrrolidone, dimethyl- or diethylaminoethyl acrylate or methacrylate, or alkyl acrylates or methacrylates, acrylamide, methacrylamide or vinyl acetate.

Among the polymers, there may be mentioned those containing units derived from carboxylic betaines, and in particular:

methyl methacrylate/ethyldimethylcarboxymethylammonium methacrylate copolymers, such as the products sold by Chimex under the name Mexomer PX (CTFA name: "polyquaternium-30") of formula:

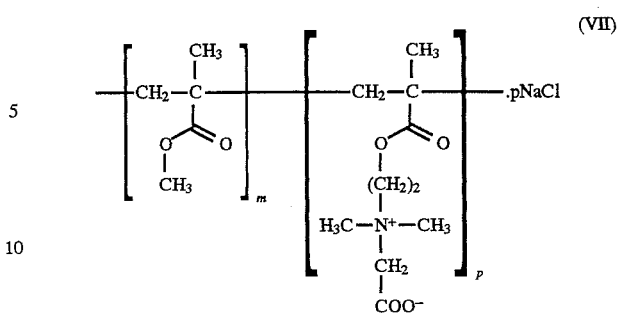

m≅60
p≅40, or similar polymers containing different proportions of the said units, the methacryloylethylbetaine/methacrylate copolymer sold by Sandoz under the name Diaformer, or the methacryloylethylbetaine/methacrylate copolymer sold by Amerchol under the name Amersette.

Among the amphoteric polymers, there may also be mentioned polysiloxane betaines, such as the polysiloxane polyorganobetaine copolymers sold by Goldschmidt under the name Abil B 9950 (CTFA Name: "Dimethicone PropylPG-Betaine") of formula:

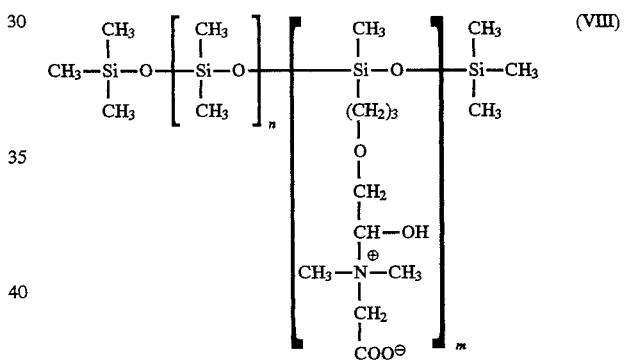

or the polydimethylsiloxane containing alkylphosphobetaine groups sold by Siltech under the name Pecosil SPB-1240, or the oxyethyleneoxypropylene organobetaine/siloxane copolymer sold by Goldschmidt under the name BC 1610.

(5) polymers derived from chitosan containing monomer units corresponding to the following formulae:

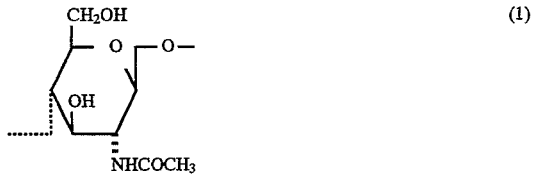

-continued

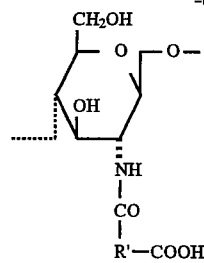  (3)

in which the units (1) are present in proportions of between 0 and 30%, the units (2) in proportions of between 5 and 50% and the units (3) in proportions of between 30 and 90%. In the formula (3), R' represents a radical of formula:

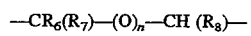

in which n is a number equal to 0 or 1, if $\underline{n}=0$, $R_6$, $R_7$ and $R_8$ each independently represent a hydrogen atom, a methyl, hydroxyl, acetoxy, amino, monoalkylamine or dialkylamine residue (optionally interrupted by one or more nitrogen atoms and/or optionally substituted with one or more amine, hydroxyl, carboxyl, alkylthio or sulphonic groups) or an alkylthio residue in which the alkyl group carries an amino substituent, at least one of the radicals $R_6$, $R_7$ and $R_8$ in this case being a hydrogen atom, or $\underline{n}$ is equal to 1, in which case $R_6$, $R_7$ and $R_8$ each represent a hydrogen atom, as well as the salts formed by these compounds with bases or acids.

Among these polymers, there may be mentioned the polymers derived from chitosan by succinylation of a certain percentage of the amino groups, such as the products sold by Chimex under the name Mexomer PAD (CTFA name: "*Chitosan Succinamide*").

(6) polymers containing units of general formula (IV):

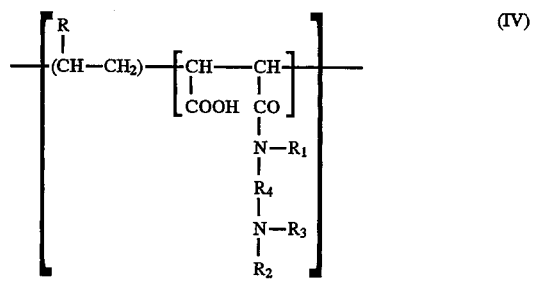  (IV)

in which R represents a hydrogen atom or a $CH_3O-$, $CH_3CH_2O-$ or phenyl radical, $R_1$ and $R_2$ independently represent a hydrogen or a lower alkyl radical such as methyl or ethyl, and $R_3$ denotes a lower alkyl radical such as methyl or ethyl or a group $-R_4-N(R_2)_2$, $R_4$ representing an alkylene group containing from 2 to 6 carbon atoms and $R_2$ being defined as above.

Such polymers are described in French Patent 1,400,366.

(7) amphoteric polymers chosen from:

the polymers obtained by the action of chloroacetic acid or sodium chloroacetate on compounds containing at least one unit of formula

  (V)

where A denotes a

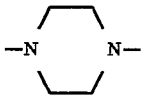

radical and the groups Z independently represent an alkylene radical containing up to 7 carbon atoms in the main chain, optionally substituted with one or more hydroxyl groups and which can contain, in addition, oxygen, nitrogen and/or sulphur atoms and/or 1 to 3 aromatic and/or heterocyclic rings, it being possible for the said oxygen, nitrogen and sulphur atoms to be present in the form of an ether, thioether, sulphoxide, sulphone, sulphonium, alkylamine, alkenylamine, hydroxyl, benzylamine, amine oxide, quaternary ammonium, amide, imide, alcohol, ester and/or urethane group;

polymers containing units of formula

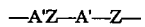  (VI)

where A' denotes a

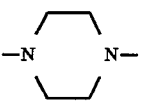

radical and where at least one of the groups Z is as defined above and at least one of the groups Z represents an alkylene radical having up to 7 carbon atoms in the main chain, optionally substituted with one or more hydroxyl radicals and containing one or more nitrogen atoms substituted with an alkyl chain optionally interrupted by an oxygen atom, and necessarily containing one or more hydroxyl and/or carboxyl functions, as well as the quaternary ammonium salts resulting from the reaction of chloroacetic acid or sodium chloroacetate with the polymers (V).

Among the amphoteric acrylic and/or methacrylic copolymers, there may also be mentioned the copolymers of ammonium chloride and acrylic acid, such as the product sold by Calgon under the name Polyquaternum-22, the acrylic block copolymer sold by Kingston under the name Hypan SS 430E or the acrylic acid/dimethyldiallylammonium chloride/acrylamide copolymer sold by Merck under the name Merquat Plus 3330, or alternatively the copolymer of dimethyldiallylammonium chloride and acrylic acid sold by Merck under the name Merquat 280.

The coated particles present in the composition of the invention are, in particular, inorganic fillers or pigments, or alternatively organic particles.

The natural or synthetic inorganic fillers are, for example, chosen from: calcium carbonates, silicates such as, for example, aluminium silicate or kaolin, calcium silicates, sodium aluminosilicate, magnesium silicate or talc, potassium aluminosilicates or micas and hydrated magnesium aluminosilicate; sulphates such as, for example, barium sulphate, calcium sulphate; and precipitated or pyrogenic silicon dioxides, as well as silica hydrogels and aerogels.

The pigments are chosen, for example, from white pigments such as titanium dioxide or zinc oxide, and coloured pigments such as: coloured iron oxides (natural or synthetic), black, red and yellow in colour; green chromium oxides, hydrated or otherwise; Prussian blue; sodium aluminosulphosilicates and their different variants known by the name of "ultramarine" pigments; cobalt aluminate or cobalt blue and manganese violet.

The pigments can also be:

either pearlescent pigments such as titanium-coated micas (mica coated with particles of titanium dioxide) and bismuth oxychloride;

or micronized pigments of metal oxides chosen from titanium, zinc, cerium and zirconium oxides or mixtures thereof.

The pigments intended to be coated according to the invention can optionally be pigments which have undergone one or more prior surface treatments of a chemical, electronic and/or mechanical nature. They can also be composite pigments with an organic coating, such as those described below.

The organic particles intended to be coated with an amphoteric polymer, according to the invention, comprise, for example:

carmine lake, carbon black, organic lakes or insoluble sodium, potassium, calcium, barium, aluminium, zirconium or strontium salts of acid dyes such as halo acid, azo, anthraquinone, and the like, dyes. Among these lakes, special mention may be made of those known by the following names:

| | | |
|---|---|---|
| D & C Red No. | 2 | Aluminium lake |
| D & C Red No. | 3 | Aluminium lake |
| D & C Red No. | 4 | Aluminium lake |
| D & C Red No. | 6 | Aluminium lake |
| D & C Red No. | 6 | Barium lake |
| D & C Red No. | 6 | Barium/strontium lake |
| D & C Red No. | 6 | Strontium lake |
| D & C Red No. | 6 | Potassium lake |
| D & C Red No. | 7 | Aluminium lake |
| D & C Red No. | 7 | Barium lake |
| D & C Red No. | 7 | Calcium lake |
| D & C Red No. | 7 | Calcium/strontium lake |
| D & C Red No. | 7 | Zirconium lake |
| D & C Red No. | 8 | Sodium lake |
| D & C Red No. | 9 | Aluminium lake |
| D & C Red No. | 9 | Barium lake |
| D & C Red No. | 9 | Barium/strontium lake |
| D & C Red No. | 9 | Zirconium lake |
| D & C Red No. | 10 | Sodium lake |
| D & C Red No. | 19 | Aluminium lake |
| D & C Red No. | 19 | Barium lake |
| D & C Red No. | 19 | Zirconium lake |
| D & C Red No. | 21 | Aluminium lake |
| D & C Red No. | 21 | Zirconium lake |
| D & C Red No. | 27 | Aluminium lake |
| D & C Red No. | 27 | Barium lake |
| D & C Red No. | 27 | Calcium lake |
| D & C Red No. | 27 | Zirconium lake |
| D & C Red No. | 30 | Lake |
| D & C Red No. | 31 | Calcium lake |
| D & C Red No. | 33 | Aluminium lake |
| D & C Red No. | 34 | Calcium lake |
| D & C Red No. | 36 | Lake |
| D & C Red No. | 40 | Aluminium lake |
| D & C Blue No. | 1 | Aluminium lake |
| D & C Green No. | 3 | Aluminium lake |
| D & C Orange No. | 4 | Aluminium lake |
| D & C Orange No. | 5 | Aluminium lake |
| D & C Orange No. | 5 | Zirconium lake |
| D & C Orange No. | 10 | Aluminium lake |
| D & C Orange No. | 17 | Barium lake |
| D & C Yellow No. | 5 | Aluminium lake |
| D & C Yellow No. | 5 | Zirconium lake |
| D & C Yellow No. | 6 | Aluminium lake |
| D & C Yellow No. | 7 | Zirconium lake |
| D & C Yellow No. | 10 | Aluminium lake | melanin pigments derived from natural or synthetic sources and which may be obtained: (A) by oxidation of at least one indole compound, or (B) by oxidative or enzymatic polymerization of melanin precursors, or (C) by extraction of melanin from substances containing it, or (D) by culturing microorganisms.

(A) Melanin pigments can, in the first case, be obtained by oxidation of at least one indole compound chosen, in particular, from those corresponding to the formula:

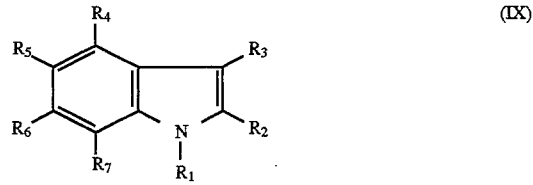

(IX)

in which:

$R_1$ and $R_3$ represent, independently of one another, a hydrogen atom or a $C_1$–$C_4$ alkyl group;

$R_2$ represents a hydrogen atom, a $C_1$–$C_4$ alkyl group, a carboxyl group or a ($C_1$–$C_4$ alkoxy)carbonyl group;

the substituents $R_4$ to $R_7$ represent a hydrogen atom, a $C_1$–$C_4$ alkyl group, a group —NHR° or —OZ, R° denoting a hydrogen atom or a $C_2$–$C_4$ acyl or $C_2$–$C_4$ hydroxyalkyl group, and the radical Z denoting a hydrogen atom, a $C_2$–$C_{14}$ acyl group, a $C_1$–$C_4$ alkyl group or a trimethylsilyl group, on the understanding that $R_5$ can, in addition, represent a halogen atom, and on the understanding that:

at least one of the radicals $R_4$ to $R_7$ represents a group OZ or NHR°, at most one of the radicals $R_4$ to $R_7$ representing NHR° and at most two of the radicals $R_4$ to $R_7$ representing OZ, and, in the case where Z represents a hydrogen atom, the two OH groups are at positions 5 and 6; and at least one of the radicals $R_4$ to $R_7$ represents a hydrogen atom and, in the case where only one of these radicals represents a hydrogen atom, only one radical among the radicals $R_4$ to $R_7$ then represents NHR° or OZ, the other radicals representing a $C_1$–$C_4$ alkyl group, or alternatively, where appropriate, for $R_5$, a halogen atom; and their alkali metal, alkaline-earth metal, ammonium and amine salts, as well as the hydrochlorides, hydrobromides, sulphates and methanesulphonates.

The indole compounds of formula (IX) above are preferably chosen from 4-hydroxyindole, 5-hydroxyindole, 6-hydroxyindole, 7-hydroxyindole, 4-hydroxy-5-methoxyindole, 4-hydroxy-5-ethoxyindole, 2-carboxy-5-hydroxyindole, 5-hydroxy-6-methoxyindole, 6-hydroxy-7-methoxyindole, 5-methoxy-6-hydroxyindole, 5,6-dihydroxyindole, N-methyl-5,6-dihydroxyindole, 2-methyl-5,6-dihydroxyindole, 3-methyl-5,6-dihydroxyindole, 2,3-dimethyl-5,6-dihydroxyindole, 2-carboxy-5,6-dihydroxyindole, 4-hydroxy-5-methylindole, 2-carboxyhydroxyindole, 6-hydroxy-N-methylindole, 2-ethoxycarbonyl-5,6-dihydroxyindole, 4-hydroxy-7-methoxy-2,3-dimethylindole, 4-hydroxy-5-ethoxy-N-methylindole, 6-hydroxy-5-methoxy-2-methylindole, 6-hydroxy-5-methoxy-2,3-dimethylindole, 6-hydroxy-2-ethoxycarbonylindole, 7-(β-hydroxy)-3-methylindole 5-hydroxy-6-methoxy-2,3-dimethylindole, 5-hydroxy-3-methylindole, 5-acetoxy-6-hydroxyindole, 5-hydroxy-2-ethoxycarbonylindole, 6-hydroxy-2-carboxy-5-methylindole, 6-hydroxy-2-ethoxycarbonyl-5-methoxyindole, 6-[N-(β-hydroxyethyl)amino]indole, 4-aminoindole, 5-aminoindole, 6-aminoindole, 7-aminoindole, N-methyl-6-hydroxyethylaminoindole, 6-amino-2,3-dimethylindole, 6-amino-2,3,4,5- tetramethylindole, 6-amino-2,3,4-trimethylindole, 6-amino-2,3,5-trimethylindole, 6-amino-2,3,6-trimethylindole, 5,6-diacetoxyindole, 5-methoxy-6-acetoxyindole, 5,6-dimethoxyindole, 5,6-methylene-dioxyindole, 5,6-trimethylsilyloxyindole, 5,6-dihydroxy-indolephosphoric ester, 5,6-dibenzyloxyindole and the addition salts of these compounds.

5,6-Dihydroxyindole is one of the preferred compounds.

The oxidation of the indole compound of formula (IX) may be performed in an aqueous or water/solvent(s) medium, in the air, in the presence or absence of an alkaline agent and/or of a metallic oxidation catalyst such as, for example, cupric ion.

The reaction medium preferably consists of water and can, where appropriate, consist of a mixture of water and at least one solvent chosen in such a way that it rapidly solubilizes the indole compound of formula (IX). Among the solvents, there may be mentioned, as examples, $C_1$–$C_4$ lower alcohols such as ethyl alcohol, propyl or isopropyl alcohol, tert-butyl alcohol, alkylene glycols such as ethylene glycol and propylene glycol, alkylene glycol alkyl ethers such as ethylene glycol monomethyl, monoethyl and monobutyl ethers, propylene glycol and dipropylene glycol monomethyl ethers, and methyl lactate.

The oxidation may also be performed using hydrogen peroxide in the presence of an alkaline agent such as, preferably, ammonia solution, or in the presence of an iodide ion, the iodide preferably being an alkali metal or alkaline-earth metal iodide or ammonium iodide.

It is also possible to perform the oxidation using periodic acid and its derivatives and water-soluble salts, permanganates and dichromates, for example sodium or potassium permanganates and dichromates, sodium hypochlorite, potassium ferricyanide, ammonium persulphate, silver oxide, lead oxide, ferric chloride, sodium nitrite, rare-earth salts including, in particular, those of cerium, and organic oxidizing agents chosen from Ortho-and parabenzoquinones, ortho-and para-benzoquinone mono- or diimines, 1,2- and 1,4-naphthoquinones and 1,2- and 1,4-naphthoquinone mono- or diimines as are defined in Application EP-A-O0,376,776. The preferred periodic acid salt is sodium periodate.

It is possible to activate the oxidizing agents with a pH modifier.

It is also possible to perform an enzymatic oxidation.

The insoluble product is isolated by filtration, centrifugation, lyophilization or atomization; it is then ground or micronized to achieve the desired particle size.

(B) Melanin pigments can also originate from the oxidative or enzymatic polymerization of melanin precursors such as L-tyrosine, L-dopa, catechol and their derivatives.

(C) melanin pigments can, also, originate from the extraction of melanin from natural substances such as human hair or the ink of cephalopods (cuttlefish, octopus), which is also known by the name of sepiomelanin, in which case the pigment is ground and purified before use.

(D) Melanin pigments may be obtained by culturing microorganisms. These microorganisms produce melanin either naturally, or by genetic modification or mutagenesis. Methods of preparation of these melanins are described, for example, in Patent Application WO 90/04029.

The melanin pigment may be present at the surface, or incorporated in a lamellar or non-lamellar, inorganic or organic particulate filler, coloured or otherwise. Composite melanin pigments are thereby obtained.

In this case, the melanin pigment can result from the oxidation of at least one indole compound of formula (IX) as defined above, mixed with the particulate filler, in a medium which is essentially a non-solvent for the said filler, at a temperature which can range from room temperature to approximately 100° C., or can alternatively result from the oxidative polymerization of melanin precursor on the filler.

The non-lamellar inorganic particles used in this process are, in particular, inert inorganic particles having a particle size of less than 20 micrometers. Such particles are, in particular, particles of calcium carbonate, silica or titanium oxide.

Such composite melanin pigments deposited on inorganic fillers are described, together with their preparation, in Patent Application FR-2,618,069.

By a similar process, composite melanin pigments with coloured inorganic particles may be prepared.

The term "coloured inorganic particles" denotes non-white particles consisting of metal salts which are insoluble in the cosmetic medium and usable in cosmetics, such as those listed in the Colour Index under the heading "Inorganic Colouring Matters" and bearing the numbers 77000 to 77947, excluding white pigments and particles occurring in lamellar form such as lamellar iron oxide. These coloured inorganic particles can consist of a single pigment or a mixture of pigments, and can thus take the form of pearlescent or interferential pigments.

The coloured inorganic particles are, in particular, non-white particles, preferably chosen from iron oxides excluding lamellar iron oxide, ultramarine blue (which is a complex sulphosilicate), chromium oxides, manganese violet (which is an ammonium manganese pyrophosphate) and Prussian Blue (which is an iron ferrocyanide).

Such composite melanin pigments, deposited on a coloured inorganic filler, are described in French Patent Application 92/0415 filed on 16th Jan. 1992.

The lamellar particles are inorganic or organic particles which take the form of lamellae, where appropriate stratified. These lamellae are characterized by a thickness which is smaller than the largest dimension of the particle. Preferably, the ratio of the largest dimension to the thickness is between 2 and 100. The largest dimension is generally less than 50 micrometers. Such composite melanin pigments deposited on a lamellar filler are described, together with their preparation, in European Patent Application No. 467, 767.

The non-lamellar organic particles are particles of inert polymers chosen from natural or synthetic organic or inorganic polymers having a crystalline or amorphous crosslinked lattice and, for example, a molecular weight of between 5,000 and 5,000,000. Composite melanin pigments on a polymeric filler, together with their preparation, are described in European Patent Application No. 379,409;

the particles obtained by oxidative polymerization of at least one indolene compound of formula:

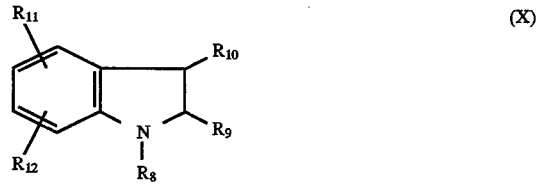

in which formula:

$R_{10}$ and $R_8$ represent, independently of one another, a hydrogen atom or a $C_1$–$C_4$ alkyl radical;

$R_9$ represents a hydrogen atom, a $C_1$–$C_4$ alkyl radical or a carboxyl or ($C_1$–$C_4$ alkoxy ) carbonyl group;

$R_{12}$ denotes a hydrogen atom, a $C_1$–$C_4$ alkyl, hydroxyl, $C_1$–$C_4$ alkoxy, amino or $C_1$–$C_{10}$ alkylamino radical or halogen;

$R_{11}$ denotes a hydrogen atom or a hydroxyl, $C_1$–$C_4$ alkoxy or amino group; with the proviso that at least one of the radicals $R_{11}$ or $R_{12}$ denotes a hydroxyl, alkoxy or amino group; and with the proviso that, when $R_{11}$ denotes an amino group, $R_{12}$ cannot denote an alkylamino radical;

it also being possible for $R_{11}$ and $R_{12}$ to form a $C_1$–$C_2$ alkylenedioxy group when they are at positions 5 and 6; and their salts.

The compounds corresponding to the formula (X) are chosen, in particular, from the group consisting of 5,6-dihydroxyindoline, 6-hydroxyindoline, 5,6-methylenedioxyindoline, 7-methoxy-6-hydroxyindoline, 6,7-dihydroxyindoline, 5-hydroxy-4-methoxyindoline, 4,5-dihydroxyindoline, 5-methoxy-6-hydroxyindoline, 4-hydroxy-5-methoxyindoline, 5-hydroxy-6-methoxyindoline, 4,7-dihydroxyindoline, 6-aminoindoline, N-ethyl-4-hydroxyindoline, 1-ethyl-6-aminoindoline, 5-6-diaminoindoline, 1-methyl-6-aminoindoline, 2-methyl-6-aminoindoline, 3-methyl-6-aminoindoline, 2-methyl-5,6-diaminoindoline, 5-chloro-7-aminoindoline, 3-methyl-5,7-diaminoindoline, 5,7-diaminoindoline, 2-methyl-5,7-diaminoindoline, 7-aminoindoline, 2-methyl-7-aminoindoline, 4-aminoindoline, 4-amino-6-chloroindoline, 4-amino-6-iodoindoline, 4-amino-5-bromoindoline, 4-amino-5-hydroxyindoline, 4-amino-5-hydroxyindoline, 4-amino-5-methoxyindoline, 4-amino-7-methoxyindoline, 5-aminoindoline, 2,3-dimethyl-5-aminoindoline, 1-methyl-5-aminoindoline, 2-methyl-5-aminoindoline, 5-[-N-(1-methylhexyl)amino]-indoline, 5,6-dimethoxyindoline and 5,6-dihydroxy-2-carboxyindoline.

In the compounds of formula (X), $C_1$–$C_4$ alkyl radicals preferably denote methyl, ethyl, propyl, isopropyl, butyl, isobutyl; $C_1$–$C_{10}$ radicals preferably denote methyl, ethyl, propyl, isopropyl, butyl, isobutyl, 1-methylhexyl, 1-methylheptyl, 1-methyloctyl; the alkoxy radicals preferably denote methoxy, ethoxy, propoxy and butoxy; halogen preferably denotes bromine, chlorine or iodine.

The salts of the compounds of formula (X) are, in particular, hydrochlorides, hydrobromides, sulphates, methanesulphonates or alkali metal, alkaline-earth metal, ammonium or amine salts.

the particles obtained by co-oxidation of at least one indoline compound of formula (X) and at least one indole derivative. The latter may be chosen from mono- and dihydroxyindoles or aminoindoles, as are described, more especially, in Patent EP-A-2,398,826 and Patent Applications EP-A-425,345 and GB-A-2,224,754.

These indoles correspond more especially to the formula (IX). During the co-oxidation, it is possible to use up to 50% mol % of indole derivatives relative to the total number of moles of derivatives to be oxidized. The oxidation conditions are identical to those of the melanin pigments described above.

Just as in the case of the melanin pigments, the products originating from the oxidative polymerization of at least one indoline compound of formula (X) can be present at the surface of a particulate filler, or incorporated in the said lamellar or non-lamellar, inorganic or organic particulate filler, coloured or otherwise. They are then composite pigments.

The inorganic particulate fillers are those mentioned above for the composite melanin pigments.

The non-lamellar organic fillers are chosen from particles of:

a) polymers derived from keratin, which are optionally modified;

b) silk fibroins;

c) polymers derived from chitin, which are optionally deacetylated;

d) cellulose polymers;

e) synthetic polymers chosen from:
 (i) polyethylene, polypropylene, polystyrene, poly(methyl methacrylate), optionally crosslinked;
 (ii) crosslinked poly-β-alanine;
 (iii) crosslinked styrene/divinylbenzene, methyl methacrylate/ethylene glycol dimethacrylate or vinyl stearate/divinylbenzene polymers;
 (iv) hollow microspheres of copolymers of vinylidene chloride and acrylonitrile;
 (v) porous microspheres of polyamide-12, polyamide-6 or copolyamide-6/12;
 (vi) silicone powders consisting, in particular, of organosiloxane elastomers, gums or resins.

Such non-lamellar organic fillers are mentioned, in particular, in European Patent Application No. 379,409.

The lamellar fillers are chosen from L-lauroyl-lysine, microparticles of ceramic, optionally coated with zirconium powder, lamellar titanium dioxide, lamellar talc, boron nitride, lamellar mica, bismuth oxychloride and transparent red iron oxide.

Such lamellar fillers are mentioned, in particular, in European Patent Application No. 467,767.

Such composite pigments, together with their preparation, are described, in particular, in French Patent Application No. 92/00417 filed on 16th Jan. 1992.

In the compositions of the invention, the proportions of the coated particles dispersed in the binding agent depend on the type of composition; these proportions are the usual ones for the type of composition in question.

To coat the particles, a known method may be used, for example one of the following methods:

1) A solution of the polymer in one of its good solvents is prepared. The powder to be coated is dispersed in this solution with vigorous stirring, and a poor solvent for the polymer is added without going to the point of precipitation of the polymer in the solution, but to the point of initial cloudiness. The suspension is then left stirring vigorously, for example for 4 hours. The suspension is allowed to settle, and the product is separated, rinsed with a non-solvent for the polymer and dried, for example at 80° C. under reduced pressure.

2) A solution of the polymer is prepared, in which the powder to be coated is dispersed. The system is left stirring vigorously, and a precipitant for the polymer is added slowly so as to cause the polymer to precipitate gently at the surface of the powder. The suspension is allowed to settle, and the powder is separated, rinsed with a non-solvent for the polymer and dried.

3) A solution is prepared with a good solvent for the polymer, and the powder to be coated is dispersed therein. A poor solvent for the polymer is chosen, the boiling point of which is above that of the good solvent, and a slow evaporation of the system is carried out. This leads to the formation of a coacervate which gradually coats the powder, and the powder is then dried.

4) The so-called air-fluidized bed technique is used; a dilute solution of the polymer is sprayed in the heated state into a cyclone, in which the powder is kept buoyant.

5) A solution of the polymer is prepared, in which the powder to be coated is dispersed. The system is left stirring vigorously, and the solvent is evaporated slowly so as to cause the polymer to precipitate gently at the surface of the powder. The suspension is allowed to settle, and the powder is separated, rinsed with a non-solvent for the polymer and dried.

6) The technique of coating by atomization is used. A suspension of particles in water is prepared; when the suspension is homogenized, an aqueous solution of the polymer is introduced into it. The mixture is left stirring for 2 hours and the suspension is atomized in an atomizing apparatus. During the atomization, the mixture is preferably kept stirring magnetically.

7) The technique of coating by lyophilization is used. To this end, the polymer is solubilized in water, and an aqueous suspension of particles is then incorporated therein with magnetic stirring. The suspension is left stirring magnetically for 6 to 8 hours, and the mixture is then placed in the lyophilizer for at least 18 hours. A pulverulent product is recovered and sieved.

In the compositions of the invention, the binding agent in which the coated particles are dispersed is a standard binding agent. The binding agents are chosen, for example, from fats (oils and/or waxes) or film-forming polymers.

The compositions of the invention can be anhydrous compositions. The anhydrous compositions take the form, in particular, of a compact powder, a loose powder, a lipstick or a nail varnish.

The compositions of the invention can also take the form of water-in-oil or oil-in-water type emulsions.

These compositions are prepared according to standard methods.

In the make-up compositions, the binding agent is a standard fatty binding agent consisting of an oil, a mixture of oils or a mixture of oil and wax(es).

In the lipsticks, the binding agent is also a fatty binding agent generally consisting of a mixture of high-melting point waxes (natural or synthetic), of oils (synthetic, mineral or vegetable) and of low-melting point waxes (natural or synthetic).

In the nail varnishes, the binding agent consists of the solution of a film-forming polymer and a plasticizer in the chosen organic solvent.

In the emulsions, the binding agent is a standard fatty binding agent consisting of an oil or a mixture of oils.

When the composition contains a micronized pigment of metal oxides chosen from titanium, zinc, cerium or zirconium oxides or mixtures thereof, it can constitute a composition for protecting the skin or hair against ultraviolet rays.

The invention also relates to the use, in the preparation of a cosmetic composition for the skin and the exoskeleton containing a dispersion of solid particles in a binding agent, of particles whose surface is coated with at least one amphoteric polymer. In this use, the composition, and in particular the particles, the amphoteric polymer and also the binding agent, are, in particular, as defined above.

The examples which follow illustrate the invention without, however, limiting it.

EXAMPLE 1

0.5 g of a methyl methacrylate/ethyldimethylcarboxymethylammonium methacrylate copolymer (Mexomer PX of Chimex) is introduced into 200 ml of water, and is allowed to dissolve completely.

Concomitantly, 50 g of talc are dispersed in 550 ml of water and, when the suspension is homogeneous, the above preparation is added with stirring.

The suspension is kept stirring for 24 hours. The talc is then recovered by centrifugation, dried, ground and sieved through a sieve of mesh 0.160 µm.

Elemental analysis of the organic residue indicates the presence of 0.92% of polymer deposited on the talc (percentage by weight relative to the talc).

Particles of the following were also coated according to the same procedure:
manganese dioxide,
titanium dioxide,
chromium oxide.

EXAMPLE 2

7.15 g of copolymer of acrylic acid and dimethyldiallylammonium chloride (Merquat 280 of Merck) are introduced into 200 ml of water, and the mixture is stirred until dissolution is complete.

A homogeneous suspension of 50 g of talc in 550 ml of water is added thereto, and the mixture is left stirring for 24 hours. The liquid/solid separation is carried out by centrifugation. The pellet is then dried, ground and sieved.

The talc obtained possesses a coating of 1.65% (weight %) of amphoteric polymer.

EXAMPLE 3

2.25 g of octylacrylamide/acrylate/butylaminoethyl methacrylate (Amphomer of National Starch) are introduced into 200 ml of water in the presence of 0.0915 g of (aminomethyl)propanol.

When the polymer has dissolved completely, a homogeneous suspension of 50 g of talc in 550 ml of water is added thereto. The mixture is kept stirring for 4 hours.

A non-solvent, namely 10 ml of 0.1 M HCl solution, is then introduced into the mixture, and stirring is continued for a further 20 hours. The coated talc is separated by centrifugation, drying, grinding and sieving. A powder possessing 0.68% of polymer (weight %) at its surface is thereby recovered.

In a similar manner, a talc coated with 1% of the same polymer was prepared.

EXAMPLE 4

A suspension of 10 g of talc in 100 ml of water is prepared. When this suspension is homogenized, a solution containing 0.2 g of methyl methacrylate/ethyldimethylcarboxymethylammonium methacrylate copolymer (Mexomer PX of Chimex) dissolved in 50 ml of water is introduced into it. The suspension is left stirring for 12 hours.

This suspension is atomized with a laboratory atomizer (Büchi 190 and Roucaire Atomizer) under the following conditions:
entry: 135° C.
exit: 70° C.
pump: 7 bars
suction: 7 bars
flow rate: 700 liters/hour
Atomization time: 45 minutes A coated dry powder containing 2.08% (weight %) of polymer is obtained.

The powder obtained is very light and of fluffy appearance.

EXAMPLE 5

3.18 g of methyl methacrylate/ethyldimethylcarboxymethylammonium methacrylate copolymer (Mexomer PX of Chimex) are introduced into 10 ml of water.

When the polymer has dissolved, this solution is added to a suspension of 10 g of talc in 40 ml of water.

The mixture is left stirring magnetically for 7 hours and then lyophilized for 18 hours.

The product recovered is sieved through a sieve of mesh 0.160 μm. A coated, very pulverulent powder is obtained, containing, on the basis of the results of elemental analysis, 6.94% of polymers (% by weight).

EXAMPLE 6

Coating of particles with an amphoteric silicone (Abil B 9950)

0.5 g of Abil B 9950 (Goldschmidt) is introduced into 200 ml of water, and is allowed to dissolve completely. The procedure followed thereafter is as described in Example 1.

COMPOSITION EXAMPLES

In these examples:

Sinnowax AO is the tradename of a mixture of cetyl/stearyl alcohol and polyoxyethylenated cetyl/stearyl alcohol (Henkel)

Geleol is the tradename of a mixture of glyceryl mono- and distearates (Gattefosse)

Veegum R is the tradename of a magnesium aluminium silicate (Vanderbilt)

Oramix L30 is the tradename of sodium lauroylsarcosinate (Seppic)

Blanose is the tradename of carboxymethylcellulose (sodium salt) sold by Aqualon Miglyol 812 is a mixture of caprylic/capric acid triglycerides (Henkel)

Imwitor 780K is a mixture of isosteric acid mono- and diglycerides esterified with succinic acid (marketed by Huls-France).

| | |
|---|---|
| Talc coated with 1% of Amphomer (Ex. 3) | 22.9% |
| Mica | 22.0% |
| Bismuth oxychloride | 8.0% |
| Titanium dioxide | 2.0% |
| Zinc stearate | 3.0% |
| Nylon-12 | 20.0% |
| Iron oxides | 15.6% |
| Binding agent | 6.5% |

The binding agent contains (% by weight):

oleyl alcohol 11%
petroleum jelly 11%
liquid paraffin 67%
isopropyl myristate 11%

To prepare this eyeshadow, the procedure is as follows.

The particulate fillers other than iron oxides are homogenized using a Baker-Perkin type decaking stirrer. The iron oxides are then added, followed by the binding agent.

In the same manner, eyeshadows were prepared containing a talc coated, respectively, with:

1% of Mexomer PX
5% of Merquat 280.

A similar control eyeshadow, but containing uncoated talc, was also prepared.

On these eyeshadows, a sensory appraisal test was carried out using a jury of 10 people, with evaluation of the following features:

adhesion of the eyeshadow at the time of application to the eyelid,
covering power of the eyeshadow immediately after making up,
staying power of the eyeshadow four hours after making up. This involves evaluating the possible presence and the extent of streaking on the eyelids, corresponding to migration of the product towards preferential areas of the eyelid.

The results of the test are as follows:

The formulae employing the coated talc were judged superior to the control, on the three criteria listed, by 7 people out of 10.

It should be noted that the best results on these three criteria were obtained with the amphoteric polymers which carry their negative and positive charges on two different side-chain substituents (e.g. Amphomer and Merquat 280).

EXAMPLE C2

Oil/water emulsion into which 5% of manganese violet coated with Mexomer PX has been introduced.

This example demonstrates the ease of dispersion of manganese violet coated with an amphoteric polymer in an emulsion. Formulation used:

| | |
|---|---|
| Fatty phase | |
| Sinnowax AO | 7% |
| Geleol | 2% |
| Cetyl alcohol | 1.5% |
| Polydimethylsiloxane | 1.5% |
| Butyl p-hydroxybenzoate | 0.2% |
| Liquid petrolatum | 15% |
| Pigment | |
| Manganese violet coated with 1% of Mexomer PX | 5% |
| Aqueous phase | |
| Glycerol | 20% |
| Water | 47.6% |
| Imidazolidinylurea (preservative) | 0.2% |

The polydimethylsiloxane is the compound sold under the name Silbione Oils 70047 V300 (Rhône-Poulenc).

The emulsion is prepared according to a traditional procedure: the pigments are introduced into the aqueous phase and the emulsion is prepared by introducing the fatty phase into the aqueous phase.

By comparison with a control emulsion containing the same percentage of uncoated manganese violet, the use of the emulsion containing the coated manganese violet is easier. This pigment disperses better. Observation of the emulsion under the microscope shows a more homogeneous dispersion of the coated pigment than in the case of the same pigment uncoated.

EXAMPLE C3

Make-up foundation containing 10.7% of titanium dioxide coated with Mexomer PX.

Formula used:

| | |
|---|---|
| PHASE A: | |
| Water | 30.34% |
| Methyl p-hydroxybenzoate | 0.1% |
| Propylene glycol | 2% |
| Black iron oxide | 0.5% |
| Titanium dioxide coated with 1% of Mexomer PX | 10.2% |
| Veegum R | 1% + 10 g of water |

-continued

| | |
|---|---|
| Blanose | 0.16% + 10 g of water |
| Oramix L30 | 0.6% |
| Triethanolamine | 1% |
| PHASE B: | |
| Stearic acid | 2.2% |
| Geleol | 2.2% |
| Miglyol 812 | 15% |
| Propyl p-hydroxybenzoate | 0.1% |
| Cyclopentadimethylsiloxane (Dow Corning 24 S Fluid) | 12% |
| PHASE C | |
| Water | 1% |
| Imidazolidinylurea | 0.3% |
| Glycerol | 3% |

Phase A is prepared in the heated state (80° C.) with stirring, Phase B is introduced into it with stirring and Phase C is added thereto. The mixture is cooled. A pinkish, fluid make-up foundation is obtained.

Observation of this emulsion under the microscope, compared to the control composition (similar but containing uncoated titanium dioxide), shows a much more even dispersion.

EXAMPLE C4

Formulation of a silicone-containing make-up foundation in which all the pigments are coated with an amphoteric silicone: Abil B 9950 of Goldschmidt.

| | |
|---|---|
| Aluminium flakes coated with a coloured epoxy varnish (Kingston Avocado M.I. Synthecolor) | 5% |
| Cyclopentadimethylsiloxane (Volatile Silicone 7158, Union Carbide) | 15% |
| Miglyol 812 | 4% |
| Imwitor 780K | 2% |
| Yellow iron oxide coated with 1% of Abil B 9950 | 1.43% |
| Red iron oxide coated with 0.5% of Abil B 9950 | 0.55% |
| Black iron oxide coated with 1% of Abil B 9950 | 0.23% |
| Titanium dioxide coated with 0.5% of Abil B 9950 | 4.80% |
| Water | 34.50% |
| Blanose 7 LF (Aqualon) | 0.50% |
| Glycerol | 15% |
| Methyl p-hydroxybenzoate | 0.2% |
| Water | 6% |
| Water | 5.8% |
| Hydrated magnesium sulphate, 7H$_2$O | 0.7% |
| Water | 7% |
| Imidazolidinylurea (Biopur 100, Biophil) | 0.3% |
| Mixture of polydimethylsiloxanol and cyclopentadimethylsiloxane, Dow Corning QC F2-1671 (Dow Corning) | 4% |

By comparison with the same formula containing the pigments coated with 5% of PDMS (polydimethylsiloxane marketed by Wackherr), the above make-up foundation possesses a creamier and smoother texture and a more intense colour. The dispersion of the pigments is good, and the emulsion is fine, even and stable after centrifugation. The make-up obtained is very homogeneous.

What is claimed is:

1. Cosmetic composition for the skin or the exoskeleton comprising a dispersion of solid particles in a binding agent, wherein at least a part of said particles is introduced into said composition in the form of particles whose surface is coated with at least one amphoteric polymer, said amphoteric polymer containing both cationic and anionic groups or containing groups which can ionize to cationic and anionic groups or combinations thereof.

2. Composition according to claim 1, wherein said cationic groups, or groups which can ionize to cationic groups, are selected from the group consisting of primary, secondary, tertiary and quaternary amine groups.

3. Composition according to claim 1, wherein said cationic groups, or groups which can ionize to cationic groups, are carried by a side-chain substituent of the polymer chain.

4. Composition according to claim 1, wherein said anionic groups are selected from the group consisting of COO–, SO$_3$–, PO$_4$– and SO$_4^{2-}$ groups.

5. Composition according to claim 1, wherein said anionic groups are carried by a side-chain substituent.

6. Composition according to claim 1, wherein said anionic and cationic groups are each carried by a side-chain substituent.

7. Composition according to claim 1, wherein the ratio of cationic groups to anionic groups ranges from 40:60 to 90:10.

8. Composition according to claim 1, wherein the weight proportion of amphoteric polymers in the coated particles is less than 10% relative to the total weight of the coated particles.

9. Composition according to claim 8 claim, wherein the said proportion does not exceed 2% by weight.

10. Composition according to claim 1, wherein said coated particles comprise inorganic fillers or pigments.

11. Composition according to claim 1, wherein said coated particles comprise organic pigments or composite pigments with an organic coating.

12. Composition according to claim 1, wherein the binding agent is selected from the group consisting of oils, waxes and film-forming polymers.

13. Composition according to claim 1, in the form of a water-in-oil or oil-in-water type emulsion.

14. A compact powder, a loose powder, a lipstick or a nail varnish comprising a composition according to claim 1.

15. A process for preparing a cosmetic composition for the skin or the exoskeleton, said composition containing a dispersion of solid particles in a binding agent, comprising adding to said composition particles whose surface is coated with at least one amphoteric polymer.

16. Cosmetic composition for the skin or the exoskeleton comprising a dispersion of solid particles in a binding agent, characterized in that at least a part of said particles is introduced into said composition in the form of particles whose surface is coated with at least one amphoteric polymer, said amphoteric polymer containing both cationic and anionic groups or containing groups which can ionize to cationic and anionic groups or combinations thereof and said amphoteric polymer is free of silicone.

17. Composition according to claim 16, wherein said cationic groups, or groups which can ionize into cationic groups, are selected from the group consisting of primary, secondary, tertiary, and quaternary amine groups.

18. Composition according to claim 16, wherein said cationic groups, or groups which can ionize into cationic groups, are carried by a side-chain substituent of the polymer chain.

19. Composition according to claim 16, wherein said anionic groups are selected from the group consisting of COO−, $SO_3^-$, $PO_4^{3-}$ and $SO_4^{2-}$ groups.

20. Composition according to claim 16, wherein said anionic groups are carried by a side-chain substituent.

21. Composition according to claim 20, wherein said anionic and cationic groups are each carried by a side-chain substituent.

22. Composition according to claim 16, wherein the ratio of cationic groups to anionic groups ranges from 40:60 to 90:10.

23. Composition according to claim 16, wherein the weight proportion of amphoteric polymers in the coated particles is less than 10% relative to the total weight of the coated particles.

24. Composition according to claim 16, wherein the weight proportion of amphoteric polymers in the coated particles is less than 8% relative to the total weight of the coated particles.

25. Composition according to claim 1 wherein the weight proportion of amphoteric polymers in the coated particles is less than 8% relative to the total weight of the coated particles.

26. Composition according to claim 24 wherein said proportion does not exceed 2% by weight.

27. Composition according to claim 16, wherein the coated particles comprise inorganic fillers or pigments.

28. Composition according to claim 16, wherein said coated particles comprise organic pigments or composite pigments with an organic coating.

29. Composition according to claim 16, wherein the binding agent is selected from the group consisting of oils, waxes and film-forming polymers.

30. Compact powder, a loose powder, a lipstick or a nail varnish comprising a composition according to claim 16.

31. A water-in-oil or oil-in-water type emulsion comprising a composition according to claim 16.

* * * * *